United States Patent [19]

Regnier et al.

[11] Patent Number: 4,968,705
[45] Date of Patent: Nov. 6, 1990

[54] BENZOPYRROLIDINONE COMPOUNDS AS BRONCHOSPASTIC AGENTS

[75] Inventors: Gilbert Regnier, Chatenay Malabry; Alain Dhainaut, Chatou; Jacques Duhault, Croissy s/Seine; Michel Lonchampt, Chevilly Larue, all of France

[73] Assignee: Adir et Cie, Neuilly-sur-Seine, France

[21] Appl. No.: 391,936

[22] Filed: Aug. 10, 1989

[30] Foreign Application Priority Data

Aug. 19, 1988 [FR] France ................... 88 11057

[51] Int. Cl.$^5$ ................ C07D 401/00; C07D 405/00; C07D 403/00; A61K 31/455
[52] U.S. Cl. ................... 514/323; 546/201; 546/198; 514/321
[58] Field of Search ............ 546/201, 208, 198; 514/323, 326, 321

[56] References Cited

U.S. PATENT DOCUMENTS 2,695,290 11/1954 Finkelstein et al. ............ 546/201

FOREIGN PATENT DOCUMENTS 2346350 3/1977 France ................... 546/201

Primary Examiner—Mary C. Lee
Assistant Examiner—Robert C. Whittenbaugh
Attorney, Agent, or Firm—Gordon W. Hueschen

[57] ABSTRACT

New benzopyrrolidinone compounds, which can be used as medicaments and correspond to the formula

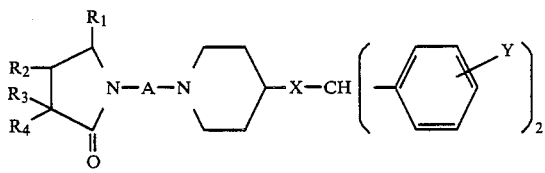

in which:
either: $R_1$ and $R_2$ together represent, with the bond of the etherocycle to which they are attached, an optionally substituted benzene nucleus and, simultaneously, $R_3$ and $R_4$ are hydrogen, $(C_1-C_4)$alkyl or $(C_5-C_6)$cycloalkyl;

or:
$R_1$ is hydrogen, $R_4$ is a single bond and $R_2$ and $R_3$ together represent, with the bond of the heterocycle to which they are bonded, an optionally substituted benzene nucleus; and A is a straight or branched hydrocarbon chain having from 2 to 6 carbon atoms that is optionally substituted by hydroxy;

X is a single bond, oxygen or sulphur; and

Y is hydrogen, halogen or $(C_1-C_5)$alkyl or alkoxy.

These new compounds and the physiologically tolerable salts thereof can be used therapeutically, especially in the treatment of bronchospastic disorders and inflammations in the ENT area.

11 Claims, No Drawings

BENZOPYRROLIDINONE COMPOUNDS AS BRONCHOSPASTIC AGENTS

The present invention relates to new benzopyrrolidinone compounds of the general formula I

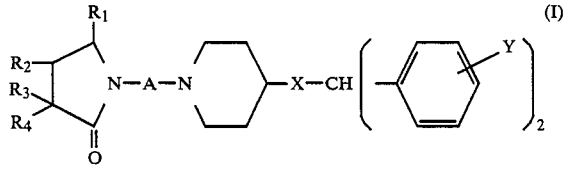

in which:
$R_1$, $R_2$, $R_3$ and $R_4$ have the following meanings:
  (a) $R_1$ and $R_2$ together represent, with the carbon-carbon bond of the heterocycle to which they are attached, a benzene nucleus that is optionally substituted by one or more halogen atoms, such as fluorine or chlorine, or by one or more trifluoromethyl, alkyl or alkoxy radicals each having from 1 to 4 carbon atoms, or by methylenedioxy:
    and, simultaneously, each of $R_3$ and $R_4$, which may be the same or different, represents a hydrogen atom, a straight chain or branched alkyl radical having from 1 to 4 carbon atoms, or a cycloalkyl radical having 5 or 6 carbon atoms;
  or
  (b) $R_1$ represents a hydrogen atom, $R_4$ represents a single bond,
    and, simultaneously, $R_2$ and $R_3$ together represent, with the carbon-carbon bond of the heterocycle to which they are attached, a benzene nucleus that is optionally substituted by one or more halogen atoms, such as fluorine or chlorine, or by one or more trifluoromethyl, alkyl or alkoxy radicals each having from 1 to 4 carbon atoms, or by methylenedioxy;
so as to form structures belonging to the indole and isoindole family of the type:

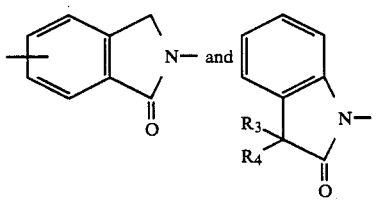

A is a straight or branched hydrocarbon chain having from 2 to 6 carbon atoms that is optionally substituted by a hydroxy radical;
X represents a single bond, or an oxygen or sulphur atom; and
Y represents a hydrogen atom or a halogen atom such as fluorine or chlorine, or an alkyl or alkoxy radical each having from 1 to 5 carbon atoms.

The prior art of the technology in this field is illustrated especially by French Patent No. 2 346 350, which relates to compounds of formula:

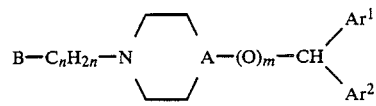

in which:
$Ar^1$ and $Ar^2$ each represents, inter alia, an optionally substituted phenyl group;
A represents:
  $>N-$ and simultaneously m is zero,
or
  22 CH— and simultaneously m is 1;
n is an integer from 2 to 6 and
—B represents, inter alia, a radical of formula:

$$\underset{R^1}{\phantom{X}}\overset{O}{\underset{}{\bigcirc}}\underset{R^2}{\phantom{X}}$$

in which:
$R_1$ and $R_2$ are hydrogen, halogen, lower alkyl or trifluoromethyl, and
Y is oxygen, sulfur or substituted nitrogen.

These compounds of the prior art are essentially antihistamines, the leading product of which is oxatomide of formula

[structure of oxatomide]

The replacement in these compounds of the prior art of group B by an oxindole or oxoisoindole group results in the compounds of the present invention, which differ from the products of the prior art in this field both in their chemical structure and their pharmacological properties.

The present invention relates also to a process for the preparation of the compounds of the general formula I which is characterised in that:
a compound of the general formula II

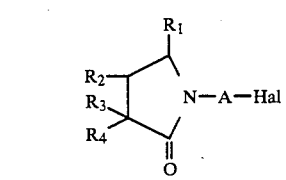

in which $R_1$, $R_2$, $R_3$, $R_4$ and A are as defined hereinbefore and Hal represents a halogen atom, such as chlorine or bromine, is condensed with a compound of the general formula III:

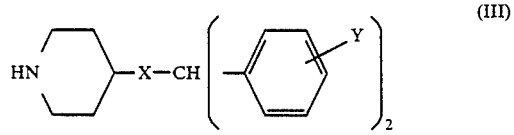

in which X and Y are as defined hereinbefore. The condensation of the compounds II and III is advantageously carried out in a polar solvent, such as an alcohol having from 2 to 4 carbon atoms, or in an aprotic solvent, such as acetonitrile or methyl ethyl ketone, at a temperature of from 80° to 100° C., in the presence of an acceptor for the hydracid formed during the course of the reaction. An excess of the compound III, an alkaline carbonate such as $K_2CO_3$ or $Na_2CO_3$, or a tertiary amine such as, for example, triethylamine, may be used as acceptor.

The products of the general formula I are bases which as such are capable of forming salts with biologically compatible organic or mineral acids. These salts are also a subject of the present invention.

The products of the general formula I may be purified by flash chromatography on a silica column (35–70μ) under a pressure of from 0.5 to 1 bar, or by crystallisation in the form of salts in appropriate solvents.

The starting materials used to prepare the compounds of the general formula I are listed in the following Tables

TABLE 1

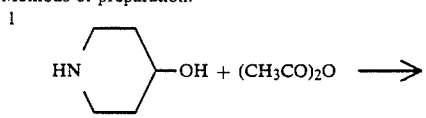

| Z | X | Y | B.p. (°C.) | M.p. (°C.) (cap) | Preparation yield en % | method |
|---|---|---|---|---|---|---|
| H | O | H | 156–167/0,2 | | 45 | 1 |
| H | O | F(4) | 155–158/0,1 | | 46,2 | 2 |
| CH₃ | S | H | 171–174/0,1 | | 78 | 3 |
| H | S | H | | 74–76 | 73 | 4 |

*Methods of preparation:

1

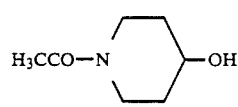

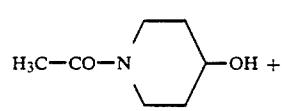

TABLE 1-continued (1) HNa/DMF (3h 80° C.)

(2) BrCH 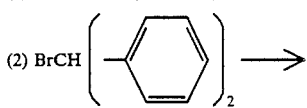

(3) concentrated solution of NaOH/EtOH (20h with heating)

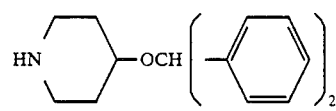

2

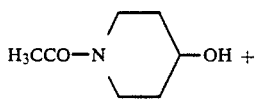

(1) HNa/DMF (3h 80° C.)

(2) BrCH 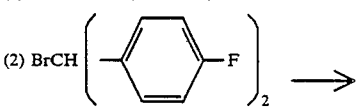

(3) NaOH/ETOH concentrated (20h with heating)

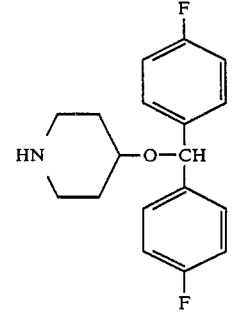

3

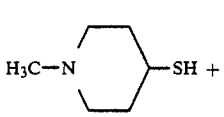

(1) EtONa/EtOH (2) BrCH 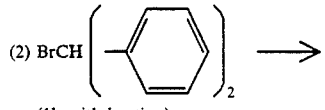

(1h with heating)

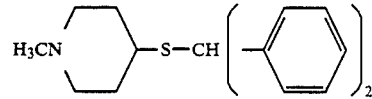

cf H. BARBERA, R. E. LYLE — J. Org. Chem., 27, 641 (1962)

4

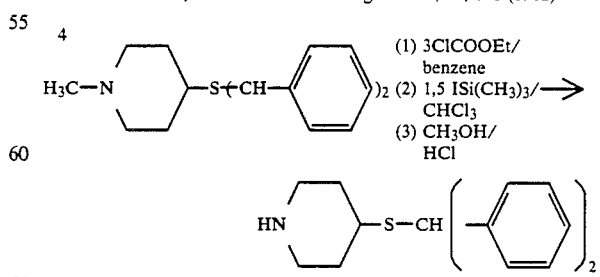

according to the method of M. E. YUNG, M. A. LYSTER, J.C.S. Chem. Comm., 315(1978)

TABLE 2

![structure: benzene ring with Z'-C(=O)-N(-(CH2)n-X) substituent and R' on ring]

| Z' | X | R' | n | B.p. (°C.) | M.p °C. | Preparation yield (in %) |
|---|---|---|---|---|---|---|
| O=C< | OH | H | 2 | | 148 (cap) | 90 |
| CH₂ | OCOCH₃ | H | 2 | oil | | 86 |
| CH₂ | Br | H | 2 | | 71 (cap) | 65 |
| >C=O | OCH₃ | H | 3 | oil | | 30 |
| CH₂ | Br | H | 3 | | 90 (cap) | 76 |
| >C=O | OH | (5) F | 2 | | 174 (K) | 76 |
| CH₂ | OCOCH₃ | (5) F | 2 | | 58 (K) | 29 |
| CH₂ | Br | (5) F | 2 | | 98–100 (cap) | 33 |
| >C=O | OH | (7) F | 2 | | 121–122 (cap) | 84 |
| CH₂ | OCOCH₃ | (7) F | 2 | | 69 (cap) | 95 |
| CH₂ | Br | (7) F | 2 | | 78 (cap) | 75 |
| >C=O | OH | (7) CF₃ | 2 | oil | | 64 |
| >C=O | OH | (5) CF₃ | 2 | | | |
| (CH₃)₂—C | OCH₃ | H | 3 | oil | | 71 |
| (CH₃)₂—C | Br | H | 3 | oil | | 75 |
| (CH₃)₂C | OCH₃ | H | 2 | oil | | 50 |
| (CH₃)₂C | Br | H | 2 | oil | | 83 |
| >=O | OCH₃ | H | 2 | | 33–38 (cap) | 93 |
| > | OCH₃ | H | 2 | oil | | 70 |
| > | Br | H | 2 | oil | | 84 |

TABLE 2-continued

Structure: Z'-C(=O)-N(-(CH2)n-X) attached to benzene ring with R' substituent

| Z' | X | R' | n | B.p. (°C.) | M.p °C. | Preparation yield (in %) |
|---|---|---|---|---|---|---|
| CH2=CH-CH(CH3)- (isobutenyl) | OCH3 | H | 3 | oil | | 41 |
| (CH3)2CH-CH2- (isobutyl) | OCH3 | H | 3 | oil | | 95 |
| (CH3)2CH-CH2- | Br | H | 3 | oil | | 90 |
| CH2=CH-CH(CH3)- | OCH3 | H | 2 | oil | | 39 |
| (CH3)2CH-CH2- | OCH3 | H | 2 | oil | | 96 |
| (CH3)2CH-CH2- | Br | H | 2 | oil | | 69 |
| cyclohexylidene | OCH3 | H | 2 | oil | | 60 |
| cyclohexyl | OCH3 | H | 2 | oil | | 94 |
| cyclohexyl | Br | H | 2 | oil | | 91 |
| (CH3)2C=O (acetonyl/C=O) | OCOCH3 | (5) F | 2 | 128 (K) | | 29 |
| CCl2 | OCOCH3 | (5) F | 2 | | | 68 |
| CH2 | OH | (5) F | 2 | 103 (K) | | 79 |
| CH2 | Cl | (5) F | 2 | 130 (K) | | 88 |
| CO | OCH3 | (5) F | 3 | 76 (K) | | 38 |
| CCl2 | OCH3 | (5) F | 3 | | | 84 |
| CH2 | OCH3 | (5) F | 3 | | | 68 |
| CH2 | Br | (5) F | 3 | | | 77 |

TABLE 3
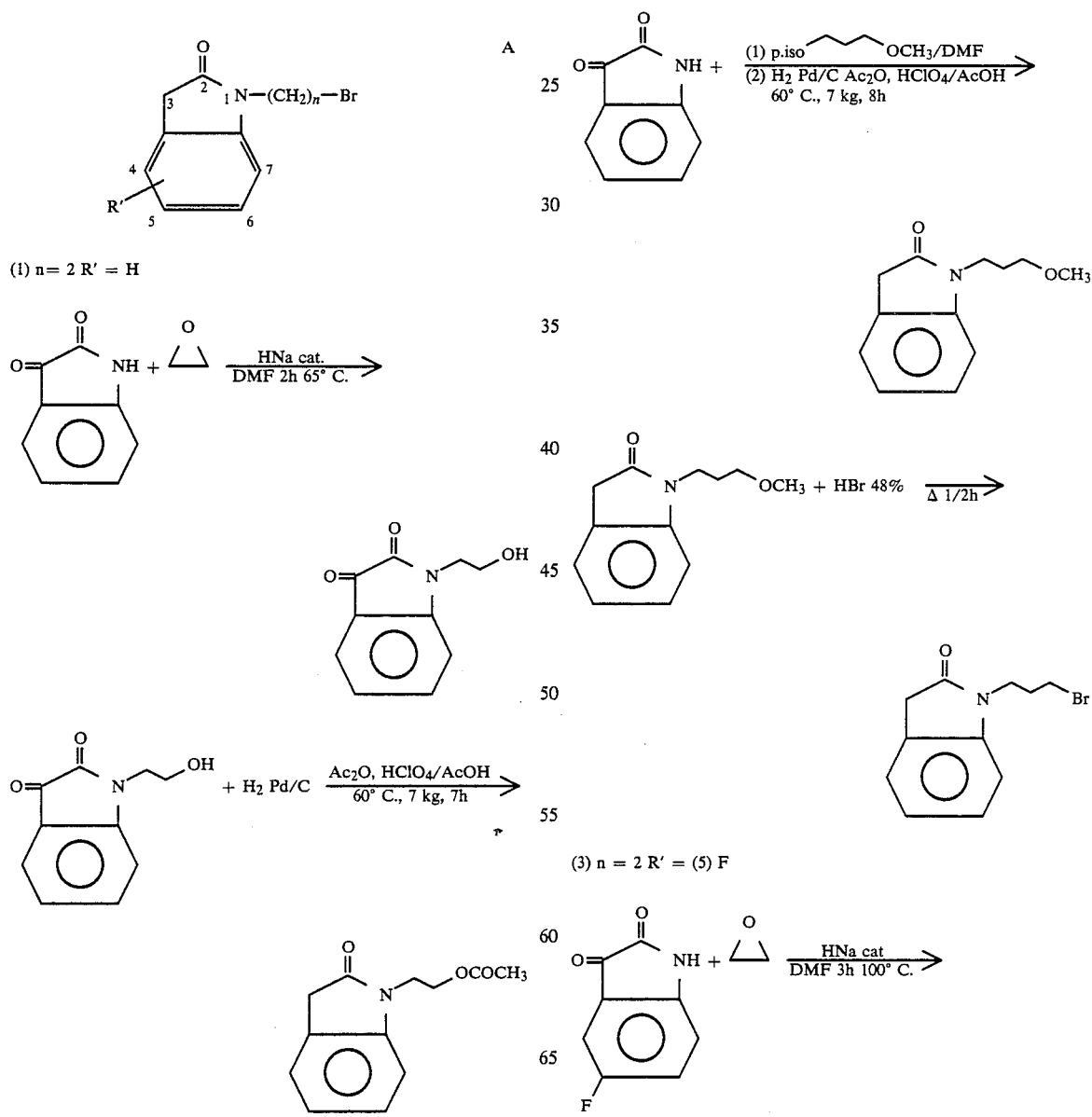
| Z' | X | R' | n | M.P. (°C.) | Preparation yield (in %) |
|---|---|---|---|---|---|
| CH$_2$ | OH | (5) F | 2 | 93–94 (cap) | 88 |
| CH$_2$ | Br | (5) F | 2 | 104–106 (cap) | 75 |
| CH$_2$ | Br | (5) F | 3 | 63–66 (cap) | 55 |
| CH$_2$ | OH | (6) F | 2 | 105–107 (cap) | 49 |
| CH$_2$ | Br | (6) F | 2 | 117–119 (cap) | 72 |
| CH$_2$ | Br | 5,6di OCH$_3$ | 3 | 111 (cap) | 57 |
Methods for preparing starting materials of formulae:
A
(1) n = 2 R' = H
(2) n = 3 R' = H
(3) n = 2 R' = (5) F

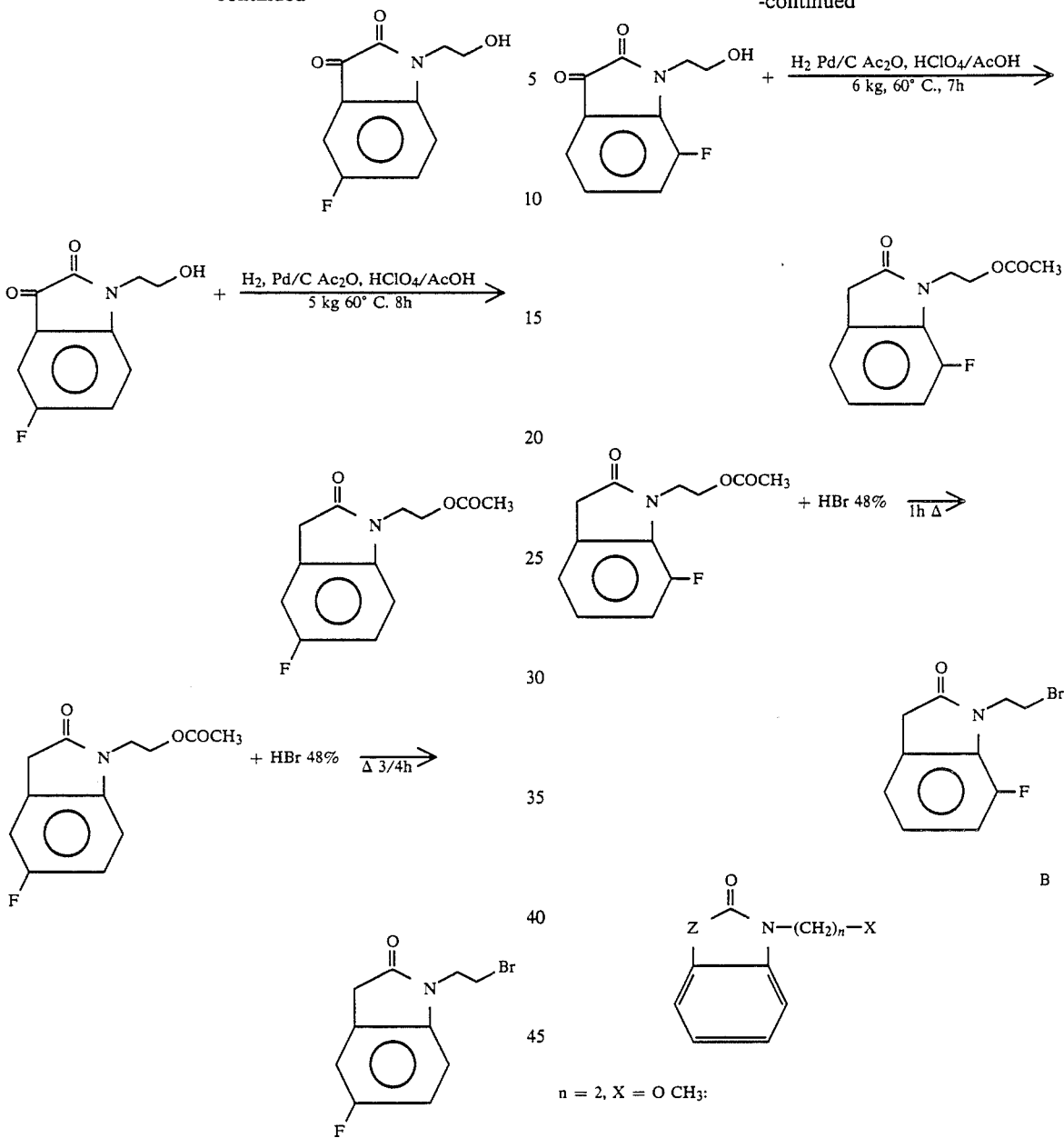
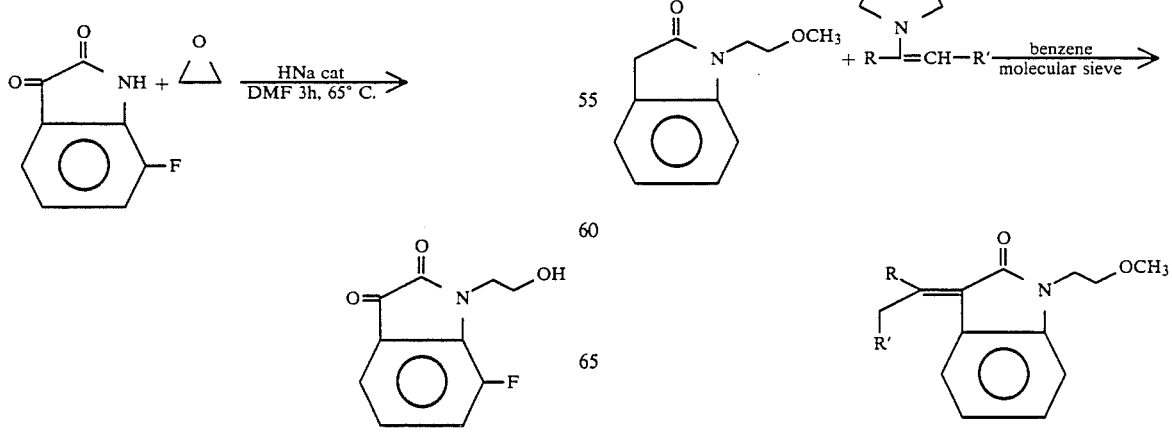
(4) n = 2 R' = (7) F

-continued

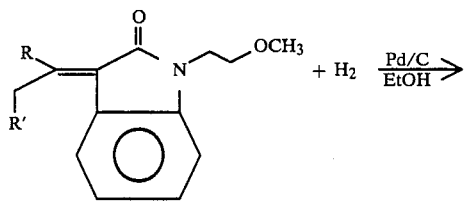

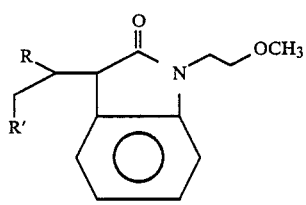

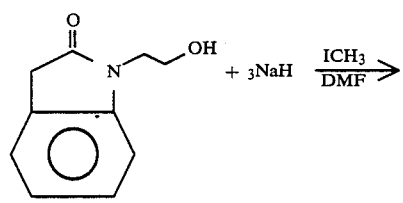

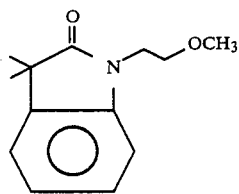

R' = H n = 2

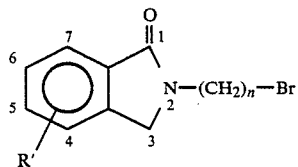

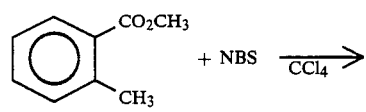

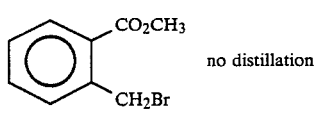

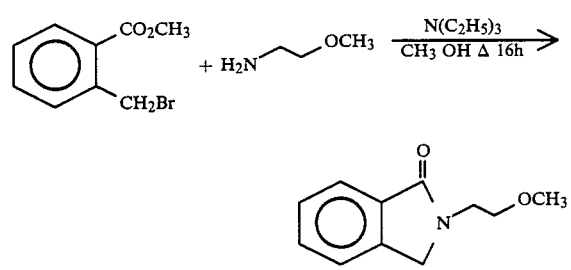

Yield = 50%
B.p.: 140–144° C./0.11

-continued

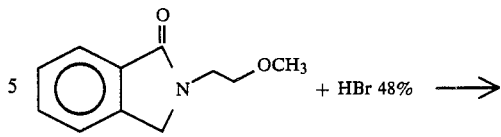

Yield = 27%, b.p.: 89° C.
R' = (5,6)di.OCH₃ n = 3

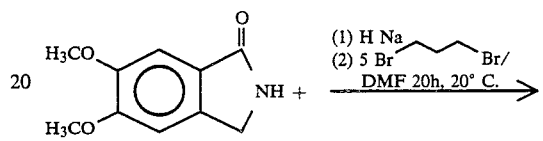

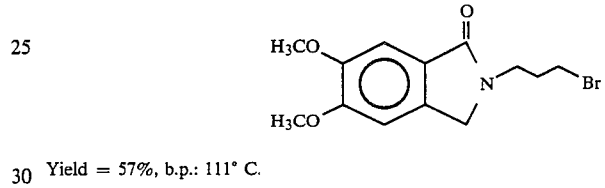

Yield = 57%, b.p.: 111° C.

The compounds of the general formula I and their physiologically tolerable salts have valuable therapeutic and pharmacological properties, especially anti-bronchoconstrictive, anti-allergic and anti-inflammatory properties, which enables them to be used as medicaments especially in the treatment of bronchospastic disorders, acute or chronic inflammatory disorders of the respiratory tract which may or may not be associated with asthmatictype manifestations of allergic or other origin, of rhinites of various origins and, more generally, of inflammations in the ENT area.

The present invention relates to pharmaceutical preparations containing as active ingredient a compound of the general formula I or a physiologically tolerable salt thereof, in admixture or association with an appropriate pharmaceutical excipient, such as, for example, distilled water, glucose, lactose, starch, talc, ethylcellulose, magnesium stearate or cocoa butter.

The pharmaceutical compositions so obtained are generally in dosage form and may contain from 10 to 250 mg of active ingredient. They may take the form, for example, of tablets, dragees, gelatin-coated pills, suppositories, injectable or drinkable solutions and, depending on the cases concerned, may be administered orally, rectally, parenterally or locally at a dose of from 10 to 250 mg from 1 to 3 times a day.

The following Examples illustrate the invention. Unless specified to the contrary, the melting points are determined using a capillary tube.

EXAMPLE 1

1-(4-benzhydryloxypiperidinoethyl)oxindole

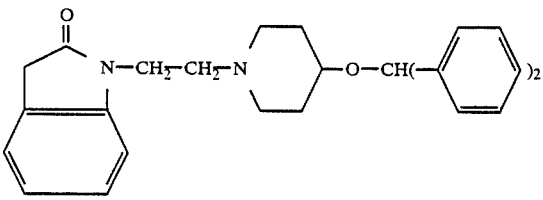

16 g of 4-benzhydryloxypiperidine (0.06 mole) and 7.2 g of N-bromoethyloxindole (0.03 mole) are heated under reflux for 16 hours in 230 ml of absolute ethanol. The mixture is concentrated to dryness, taken up in 300 ml of ether, washed with a 10% aqueous solution of Na$_2$CO$_3$, then with water. The organic solution is dried on MgSO$_4$ and concentrated. The oil remaining is purified on 450 g of silica with a mixture of CH$_2$Cl$_2$ and CH$_3$COOC$_2$H$_5$ (7:3) as eluant. The product is crystallised from a 4% solution of fumaric acid in ethanol. The fumarate of 1-(4-benzhydryloxypiperidinoethyl)oxindole is obtained, m.p.: 153°-154° C. (yield: 46%).

EXAMPLE 2

2-(4-benzhydryloxypiperidinoethyl)isoxindole

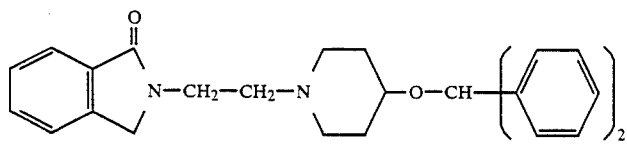

5.3 g of 4-benzhydryloxypiperidine (0.02 mole) and 2.4 g of N-bromoethylisoxindole (0.01 mole) are heated under reflux for 16 hours in 80 ml of absolute ethanol. The mixture is concentrated to dryness, taken up in 100 ml of ether, washed with a 10% aqueous solution of Na$_2$CO$_3$, then with water. The organic solution is dried on MgSO$_4$ and concentrated. The oil remaining is purified on 250 g of silica with ethyl acetate as eluant. The product is crystallised from a mixture of CH$_2$Cl$_2$ and (C$_2$H$_5$)$_2$O, yielding 2-(4-benzhydryloxypiperidinoethyl)isoxindole, m.p. 128°-129° C., (yield: 70%).

EXAMPLES 3 TO 20

The products given by way of example hereinafter were prepared in accordance with the procedure described in Example 1:

(3) 1-(4-bis-para-fluorobenzhydryloxypiperidinoethyl)oxindole, m.p. of the corresponding acid fumarate: 164°-167° C. (ethanol/ether).

(4) 1-(4-bis-para-fluorobenzhydrylpiperidinopropyl)-oxindole, m.p. of the corresponding maleate: 113° C. (ethanol/ether).

(5) 1-(4-benzhydryloxypiperidinopropyl)-oxindole, m.p. of the corresponding fumarate: 160°-161° C. (ethanol).

(6) 1-(4-benzhydryloxypiperidinoethyl)-7-fluoro-oxindole, m.p. of the corresponding fumarate: 134°-137° C. (ethanol).

(7) 1-(4-bis-para-fluorobenzhydryloxypiperidinoethyl)oxindole, m.p. of the corresponding fumarate: 172°-173° C. (ethanol).

(8) 1-(4-benzhydryloxypiperidinoethyl)-5-fluoro-oxindole, m.p. of the corresponding fumarate: 172°-173° C. (ethanol/ether). ether).

(9) 1-(4-benzhydrylthiopiperidinoethyl)-oxindole, m.p. of the corresponding fumarate: 177°-179° C. (ethanol).

(10) 1-(4-bis-para-fluorobenzhydrylpiperidinoethyl)oxindole, m.p. of the corresponding maleate: 162° C. (ethanol/ether).

(11) 2-(4-benzhydrylthiopiperidinoethyl)-isoxindole.

(12) 2-(4-benzhydryloxypiperidinopropyl)-5,6-dimethoxyisoxindole, isoxindole, M.P.: 49°-54° C. (ethanol/petroleum ether).

(13) 2-(4-benzhydryloxypiperidinoethyl)-5,6-methylenedioxyisoxindole.

(4) 1-(4-benzhydryloxypiperidinoethyl)-3,3-dimethyloxindole, M.P.: 87°-88° C. (ether/petroleum ether).

(15) 1-(4-benzhydryloxypiperidinoethyl)-3-isopropyloxindole, M.P. of the corresponding methane sulphonate : 140°-142° C. (ethanol/water).

(16) 2-(4-benzhydryloxypiperidinopropyl)-isoxindole, M.P. (K) of the corresponding hydrochloride: 232° C. (ethanol/ether).

(17) 1-(4-benzhydryloxypiperidinopropyl)-5-fluoro-oxindole, M.P. (K) of the corresponding hydrochloride: 230° C. (ethanol).

18) 2-(4-benzhydryloxypiperidinoethyl)-5-fluoro-isoxindole, M.P.: 138°-140° C. (ether).

(19) 2-(4-benzhydryloxypiperidinopropyl)-5-fluoro-isoxindole, M.P.: 82°-92° C. (ethanol/water/ether).

(20) 2-(4-benzhydryloxypiperidinoethyl)-6-fluoro-isoxindole, M.P.: 123°-124° C. (ether).

EXAMPLE 21

Pharmacological study of the compounds of the general formula I

The compounds of the invention and the prior art product fenspiride of the prior art used as reference substance were subjected to various tests described in ARZNEIMITTEL-FORSCHUNG/DRUG RESEARCH 37 (II), 12, 1354–1355 (1987), especially the histamine-induced bronchoconstriction test in guinea pigs, to the determination of the passive shock resulting from the study of experimental asthma induced in guinea pigs by antigen aerosols and to assays in vitro on the inhibition of purified phosphodiesterase.

The results obtained are listed in the following Table.

Examination of this Table shows the value of the compounds of the invention, their low toxicity and pronounced activity permitting them to be used therapeutically, especially in the respiratory and ENT fields.

| Compounds of Examples | Toxicity LD$_{50}$ mg/kg mouse | Armitage test guinea pig p.o. | | Passive shock guinea pig ED$_{50}$ mg/kg | Phosphodiesterase inhibition IC$_{50}$ | |
|---|---|---|---|---|---|---|
| | | dose mg:kg | % protection | | basal | +calmoduline |
| 1 | ~200 (IP) | 1 | +66 | 2,5 IP 5 PO | inactif | $1,8.10^{-5}$M |
| 2 | >800 (PO) | 1 | +36 | 2,5-5 (PO) | >$10^{-4}$M | $3,4.10^{-5}$M |
| 3 | <800 (PO) | 1 | +47,6 | | inactif | $2,7.10^{-6}$M |
| 4 | ~200 (IP) | 20 | +59,4 | 40 (IP) | | |
| 5 | | 1 | +72,1 | | >$10^{-4}$M | $10^{-4}$M |
| 6 | | 1 | +36.6 | | inactif | $2,5.10^{-5}$M |
| 7 | <800 (PO) | 1 | +50 | 2,5-5 (PO) | inactif | $9,9.10^{-6}$M |
| 8 | | 1 | +72 | 2,5-5 (PO) | >$10^{-5}$M | $6,8.10^{-6}$M |
| 9 | | 5 | +60 | | | |
| 10 | <800 (PO) | 5 | +78 | | >$10^{-4}$M | $10^{-4}$M |
| 12 | 800 (PO) | 5 | +79 | 20 (PO) | $7.10^{-5}$M | $2.10^{-5}$M |
| 14 | >800 (PO) | 5 | +70 | >40 (PO) | $3.10^{-5}$M | $2.10^{-5}$M |
| 15 | >800 (PO) | 5 | +50 | 5 (PO) | $10^{-4}$M | $3.10^{-5}$M |
| 16 | >800 (PO) | 5 | +82 | 5 (PO) | >$10^{-4}$M | $3.10^{-5}$M |
| 17 | >800 (PO) | 5 | +75 | 40 (PO) | >$10^{-4}$M | $10^{-5}$M |
| 18 | >800 (PO) | 5 | +68 | 40 (PO) | $10^{-4}$M | $2.10^{-5}$M |
| 19 | >800 (PO) | 5 | +68 | 10 (PO) | >$10^{-4}$M | $2.10^{-5}$M |
| 20 | >800 (PO) | 5 | +43 | 40 (PO) | >$10^{-4}$M | $2.10^{-5}$M |
| Fenspiride | >800 (PO) | 2,5 | +69 | 5 (IP) 10 (PO) | >$10^{-4}$M | >$10^{-4}$M |

The compounds of the present invention were also tested on the mice's ear edema according to the technique of John M. YOUNG et al., Journal of Investigative Pharmacology, 82, 363–371 (1984). Administrated, per os, at a dose of 36 micromole/kg, the derivatives of the present invention provoke a decrease of the mice's ear edema of from 15 to 50% according to the compounds.

In the same conditions and with the same dose: fenspiride shows no activity;

oxatomide and 1[(2-oxo-3-benzimidazolinyl-ethyl]-4-benzhydryloxy-piperidine—which are structurally the two closest Prior Art products—each give a decrease of the mice∝s ear edema lower than 15%—showing so the superiority of the compounds of the present invention on the similar products of the Prior Art.

We claim:

1. A benzopyrrolidinone compound selected from those of the formula I

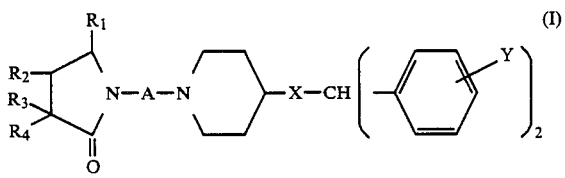

in which:

$R_1$, $R_2$, $R_3$ and $R_4$ have the following meanings:

a
$R_1$ and $R_2$ together represent, with the carbon-carbon bond of the heterocycle to which they are attached, a benzene nucleus that is unsubstituted or substituted by one or more halogen atoms, or by one or more trifluoromethyl, alkyl or alkoxy radicals each having from 1 to 4 carbon atoms, or by methylenedioxy;

and, simultaneously, each of $R_3$ and $R_4$, which may be the same or different, represents a hydrogen atom, a straight chain or branched alkyl radical having from 1 to 4 carbon atoms, or a cycloalkyl radical having 5 or 6 carbon atoms;

or b
$R_1$ represents a hydrogen atom, $R_4$ represents a single bond, and, simultaneously, $R_2$ and $R_3$ together represent, with the carbon-carbon bond of the heterocycle to which they are attached, a benzene nucleus that is unsubstituted or substituted by one or more halogen atoms, or by one or more trifluoromethyl, alkyl or alkoxy radicals each having from 1 to 4 carbon atoms, or by methylenedioxy;

so as to form structures belonging to the indole and isoindole family of the type:

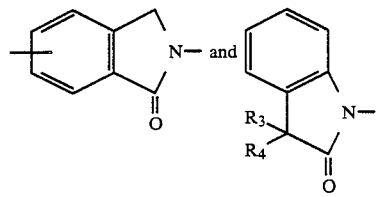

A is a straight or branched hydrocarbon chain having from 2 to 6 carbon atoms that is unsubstituted or substituted by a hydroxy radical;

X represents a single bond, or an oxygen or sulphur atom; and

Y represents a hydrogen or halogen atom, or an alkyl or alkoxy radical each having from 1 to 5 carbon atoms, and a pharmaceutically-acceptable acid-solution salt thereof.

2. A salt of a compound of claim 1 with a biologically compatible acid.

3. A compound of claim 1 which is: 1-(4-benzhydryloxypiperidinoethyl)-oxindole.

4. A compound of claim 1 which is: 2-(4-benzhydryloxypiperidinoethyl)-isoindole.

5. A pharmaceutical composition useful for treating bronchospastic disorders or inflammations in the ENT area containing as active ingredient an effective amount of a compound according to claim 1 together with an appropriate pharmaceutical excipient.

6. A method for treating a living animal body afflicted with bronchospastic disorders or inflammations in the E N T area, comprising the step of administering to the said living animal an amount of a compound of claim 1 which is effective for the alleviation of the said condition.

7. A pharmaceutical composition useful for treating bronchospastic disorders or inflammations in the ENT area containing as active ingredient an effective amount of a compound according to claim 2 together with an appropriate pharmaceutical excipient.

8. A pharmaceutical composition useful for treating bronchospastic disorders or inflammations in the ENT area containing as active ingredient an effective amount of a compound according to claim 3 together with an appropriate pharmaceutical excipient.

9. A pharmaceutical composition useful for treating bronchospastic disorders or inflammations in the ENT area containing as active ingredient an effective amount of a compound according to claim 4 together with an appropriate pharmaceutical excipient.

10. A compound of claim 1 wherein, when $R_1$ and $R_2$ together represent, with the carbon-carbon bond of the heterocycle to which they are attached, a benzene nucleus that is substituted by one or more halogen atoms, the halogen is selected from fluorine and chlorine.

11. A compound of claim 1 wherein, when $R_2$ and $R_3$ together represent, with the carbon-carbon bond of the heterocycle to which they are attached, a benzene nucleus that is substituted by one or more halogen atoms, the halogen is selected from fluorine and chlorine.

* * * * *

UNITED STATES PATENT AND TRADEMARK OFFICE
CERTIFICATE OF CORRECTION

PATENT NO. : 4,968,705

DATED : Nov. 6, 1990

INVENTOR(S) : Gilbert Regnier, Alain Dhainaut, Jacques Duhault, Michel Lonchampt It is certified that error appears in the above-identified patent and that said Letters Patent is hereby corrected as shown below:

Title Page [57] ABSTRACT, third line down after the formula; "etherocycle" should read -- heterocycle --.

Column 1, line 26; "methylenedioxy:" should read -- methylenedioxy; --.

Column 2, line 14; "22 CH" should read -- $\geq$CH --.

Column 4, 2nd formula up from the bottom "S(CH" should read -- S-(CH --.

Column 4, 2nd line up from bottom; "according" should read -- *according --.

Column 5, 1st column, 5th line up from bottom; "$(CH_3)_2 C$" should read -- $(CH_3)_2$-C --.

Column 5, 1st column, 4th line up from bottom; "$(CH_3)_2 C$" should read -- $(CH_3)_2$-C --.

Column 7, 5th column, 8th line up from bottom; move "128 (K)" to under the column "M.p °C."

Column 7, 6th column, 8th line up from bottom; move "29" to under the last column.

Column 7, 6th column, 7th line up from bottom; move "68" to under the last column.

Column 7, 5th column, 6th line up from bottom; move "103 (K)" to under the column "M.p °C."

Column 7, 6th column, 6th line up from bottom; move "79" to under the last column.

Column 7, 5th column, 5th line up from bottom; move "130 (K)" to under the column "M.p °C."

Column 7, 6th column, 5th line up from bottom; move "88" to under the last column.

Column 7, 5th column, 4th line up from bottom; move "76 (K)" to under the column "M.p °C.".

Column 7, 6th column, 4th line up from bottom; move "38" to under the last column.

UNITED STATES PATENT AND TRADEMARK OFFICE
CERTIFICATE OF CORRECTION

PATENT NO.   : 4,968,705

DATED        : Nov. 6, 1990

INVENTOR(S)  : Gilbert Regnier, Alain Dhainaut, Jacques Duhault, Michel Lonchampt It is certified that error appears in the above-identified patent and that said Letters Patent is hereby corrected as shown below:

Column 7, 6th column, 3rd line up from bottom; move "84" to under the last column.
Column 7, 6th column, 2nd line up from bottom; move "68" to under the last column.
Column 7, 6th column, last line; move "77" to under the last column.
Column 9, approximate line 24; move "A" to the left hand margin of column 9.
Column 12, approximate line 38; move "B" to the left hand margin of Column 12.
Column 13, approximate line 36; move "C" to the left hand margin of column 13.
Column 14, line 41; "asthmatictype" should read -- asthmatic-type --.
Column 16, line 6; delete "ether)." second occurrence.
Column 16, line 15; delete "isoxindole," second occurrence.
Column 17, 2nd column, 1st line; "∿200" should read --≃200 --.
Column 17, 2nd column, 4th line; "∿200" should read --≃200 --.
Column 17, line 40; "mice œ s" should read -- mice's --.

Signed and Sealed this

Nineteenth Day of May, 1992

*Attest:*

DOUGLAS B. COMER

*Attesting Officer*   Acting Commissioner of Patents and Trademarks